United States Patent
Sandstrom et al.

(10) Patent No.: US 6,613,015 B2
(45) Date of Patent: Sep. 2, 2003

(54) RIGHT ANGLE SAFETY NEEDLE

(75) Inventors: Jeffrey D. Sandstrom, Forest Lake, MN (US); William L. Beling, Newbrighton, MN (US); Kristin Finberg, Minneapolis, MN (US); Ronald G. Travis, Spring Lake Park, MN (US)

(73) Assignee: Deltec, Inc., St. Paul, MN (US)

( * ) Notice: Subject to any disclaimer, the term of this patent is extended or adjusted under 35 U.S.C. 154(b) by 39 days.

(21) Appl. No.: 09/969,870

(22) Filed: Oct. 4, 2001

(65) Prior Publication Data

US 2003/0069546 A1 Apr. 10, 2003

(51) Int. Cl.⁷ .................................................. A61M 5/00
(52) U.S. Cl. ........................ 604/110; 604/117; 604/233; 604/239; 604/272
(58) Field of Search ................................ 604/110, 117, 604/233, 239, 240, 272, 93.01

(56) References Cited

U.S. PATENT DOCUMENTS

| | | | | |
|---|---|---|---|---|
| 2,899,959 A | * | 8/1959 | Ginsburg | 604/174 |
| 4,968,303 A | * | 11/1990 | Clarke et al. | 604/187 |
| 5,395,346 A | * | 3/1995 | Maggioni | 604/195 |
| 5,858,001 A | * | 1/1999 | Tsals et al. | 604/135 |
| 6,500,150 B1 | * | 12/2002 | Gross et al. | 604/131 |

* cited by examiner

Primary Examiner—Brian L. Casler
Assistant Examiner—Jeremy Thissell
(74) Attorney, Agent, or Firm—Louis Woo (57) ABSTRACT

A right angle safety needle has a base to which an arm is hingedly mounted at a proximal portion. The base has an opening at its distal portion wherethrough the vertical portion of the right angle needle extends. A well is formed adjacent the opening and a dam is provided on the side of the well away from the opening. To retract the needle from the opening, the horizontal portion of the needle, which may be encased in an arm, is rotated about the upright to which it is hingedly connected so that the needle is pivoted upwards and withdrawn from the opening. Once the tip of the needle clears the opening, due to the tip of the needle being offset from the body of the needle and the fact that the needle tends to flex forward, the tip of the needle is entrapped in the well adjacent to the opening. The dam forward of the well provides a backstop for any further forward movement of the tip of the needle, thereby fixedly retaining the needle within the well. Stops are provided in the device, at its arm and base, to prevent the needle from being further moved relative to the base once the tip of the needle is entrapped in the well of the base.

18 Claims, 12 Drawing Sheets

RIGHT ANGLE SAFETY NEEDLE

FIELD OF THE INVENTION

The present invention relates to hypodermic needles and particularly a right angle safety needle that is to be used with infusion therapy.

BACKGROUND OF THE INVENTION

For intravenous therapy where a medicament fluid is directly introduced to the vein of a patient, a needle or some other venous access device is usually used. Conventional needles are generally used for short term treatments, as the contaminated needles are used but once. For long term treatment whereby a fluid may be repeatedly infused to the patient, the prior art teaches the use of implantable devices such as for example a port or portal that has attached thereto a catheter that routes the fluid through the port to a site remote from the implanted port. The implanted port is accessed by a needle being inserted through the patient's skin into a septum. Fluid may then be introduced through the port so as to be routed by the catheter from the port to the desired remote site. When an implanted port is used, the needle most likely is a right angle needle that needs to be changed periodically. But each time that a needle is removed, there is always the chance that the healthcare worker handling the needle may be pricked by the contaminated needle. An easy to use, yet reliable, right angle safety needle having a protective system is therefore needed for infusing fluids to a patient as for example by means of an implanted port.

One such right angle hypodermic safety needle is disclosed in Rosato et al. U.S. Pat. No. 5,951,522. The '522 safety needle uses a number of interconnected foldable flaps hung from the horizontal portion of the right angle needle. The fact that the two lowermost flaps need to be pressed together to secure the tip of the contaminated needle therebetween means that the healthcare worker's fingers could be subjected to the risk of coming into contacted with the contaminated needle. A second embodiment of the right angle safety needle disclosed in the '522 patent uses the patient's skin as a fulcrum for withdrawing the needle. The problem with the approach taught by the alternative embodiment is that it subjects the patient to unnecessary discomfort inasmuch as sufficient pressure has to be applied to the area of the patient adjacent to the needle in order to withdraw the needle from the patient.

There is therefore a need for a right angle safety needle that is simply constructed and yet is readily usable without exposing the contaminated needle to the user and at the same time causing too much discomfort to the patient.

SUMMARY OF THE INVENTION

The right angle safety needle of the instant invention utilizes a pivoting movement for withdrawing the needle from a patient. In particular, the needle of the instant invention has a base that rests planarly on the skin of a patient when the needle is to be inserted to the patient to, for example, establish a fluid communication path with a port implanted into the patient. The base has a distal end and a proximal end. An opening or aperture is provided at the distal end wherethrough the vertical portion of the right angle needle extends. The horizontal portion of the right angle needle is encased in an arm by for example being molded to a synthetic and non-allergic material such as plastic. The arm in turn is connected to a conduit wherethrough fluid is flowable.

At the proximal end of the base there is an upright, in the form of two upraised members or sidewalls to which the arm is hingedly connected, so that the arm is pivotable about the upright. The position of the right angle, or L-shaped, needle before and during use is such that the horizontal portion of the needle lies in parallel to the length of the base and the vertical portion extends through the aperture at the distal end of the base. The sharp tip of the needle is offset from the vertical needle portion, as is conventionally known. To keep the right angle needle in the aforenoted position, a holding clip is placed over the front end of the arm for securing the arm to grooves formed at a dam or backstop that extends from the distal end of the base.

After insertion, to remove the needle from the patient, the holding clip is first removed from the front end of the arm. Thereafter, the healthcare worker could either place a thumb under a front extension of the arm or simply push or pull the arm upwards so that the aft portion of the arm is pivoted about the upright at the proximal end of the base. As the arm is pivoted upwards, the vertical portion of the needle is withdrawn from the patient. Once the sharp tip of the needle clears the aperture at the distal end of the base, due to it being offset from the longitudinal axis of the vertical portion of the needle and the natural tendency of the vertical portion of the needle to return to its natural shape vis a vis the horizontal portion of the needle, the sharp tip of the needle is biased forward away from the aperture at the base and gets caught in a well or basin adjacent to the aperature. A dam or backstop circumventing the well prevents the tip of needle from any further forward movement, thereby trapping and retaining the tip of the needle in the well.

Stop portions may be provided at both the upright and the arm to ensure that the arm could only be pivoted to a predetermined angle relative to the base. This ensures that the tip of the needle, once trapped in the well, could not be further removed from the well.

To ensure that it is not just the vertical portion of the needle that prevents downward movement of the needle, a second embodiment of the instant invention provides a stop mechanism or part at either the upright or the base to prevent downward movement of the arm, once the arm has been pivoted to the predetermined angle relative to the base. Thus, with stop mechanisms that prevent the needle from further upward and downward movements, once removed from the patient and trapped in the well, the tip of the contaminated needle will remain fixedly retained in the well of the base.

It is therefore an objective of the present invention to provide a safety needle that is both convenient to use and enables a user to avoid any potential contact with the tip of a contaminated needle.

It is yet another objective of the present invention to provide a right angle safety needle system that has a construction that ensures that the tip of a needle, once trapped, will remain fixedly retained within a catch integrated to the system.

BRIEF DESCRIPTION OF THE FIGURES

The above-mentioned objectives and advantages of the present invention will become apparent and the invention itself will best be understood by reference to the following description of the present invention taken in conjunction with the accompanying drawings, wherein.

DETAILED DESCRIPTION OF THE INVENTION

With reference to FIGS. 1–5, the present invention safety needle device 2 is shown to include a base 4 that has a substantially planar lower surface 6. Adhesively attached to bottom surface 6 of base 4 is a foam padding 8 which enables device 2, and more specifically base 4 to be planarly placed against the skin 10 of a patient 12. See FIG. 3.

Figure 2:
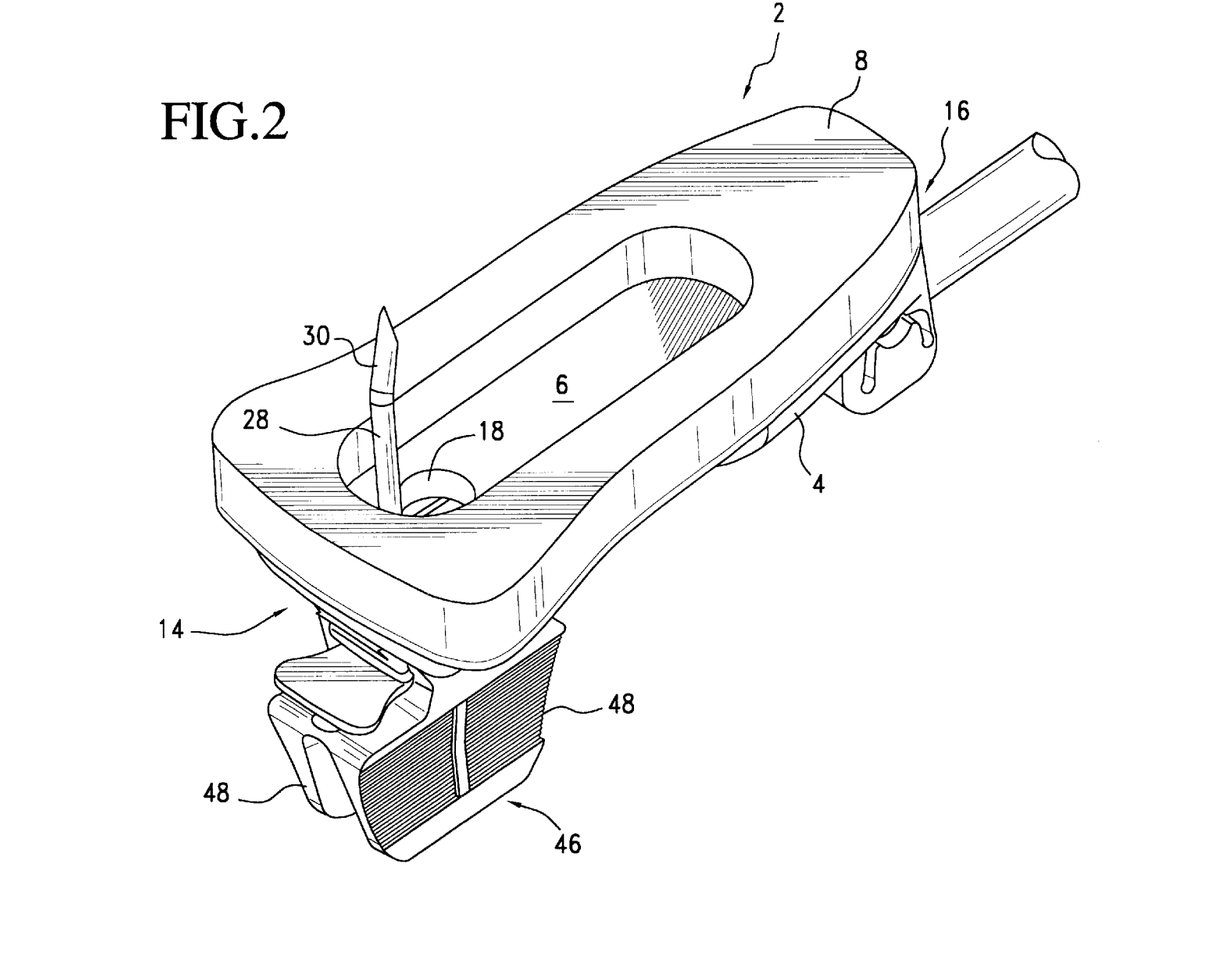
FIG. 2 is a perspective view of the device of FIG. 1 as viewed from its bottom.
Figure 5:
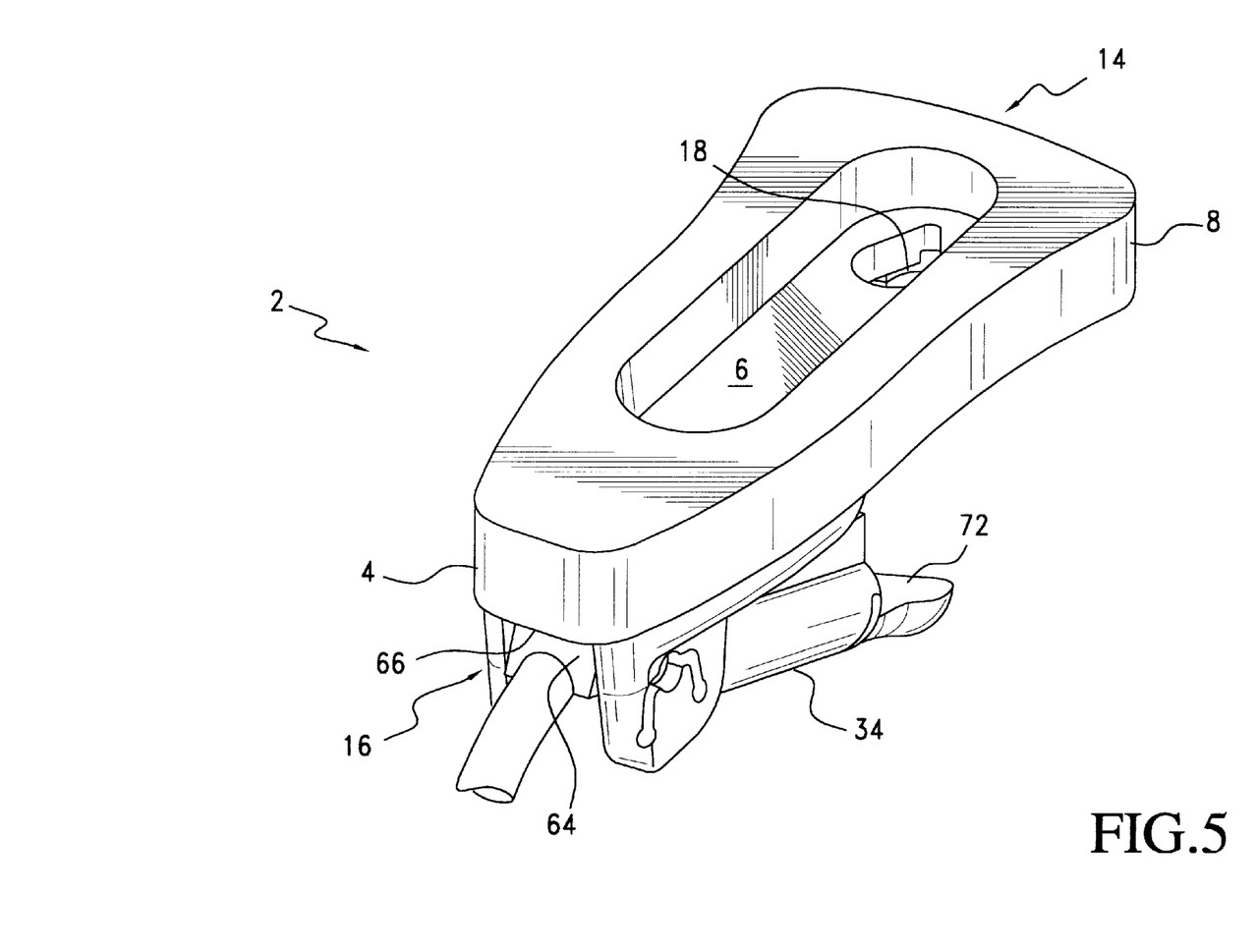
FIG. 5 is a bottom view of the device as shown in FIG. 4.
Figure 6:
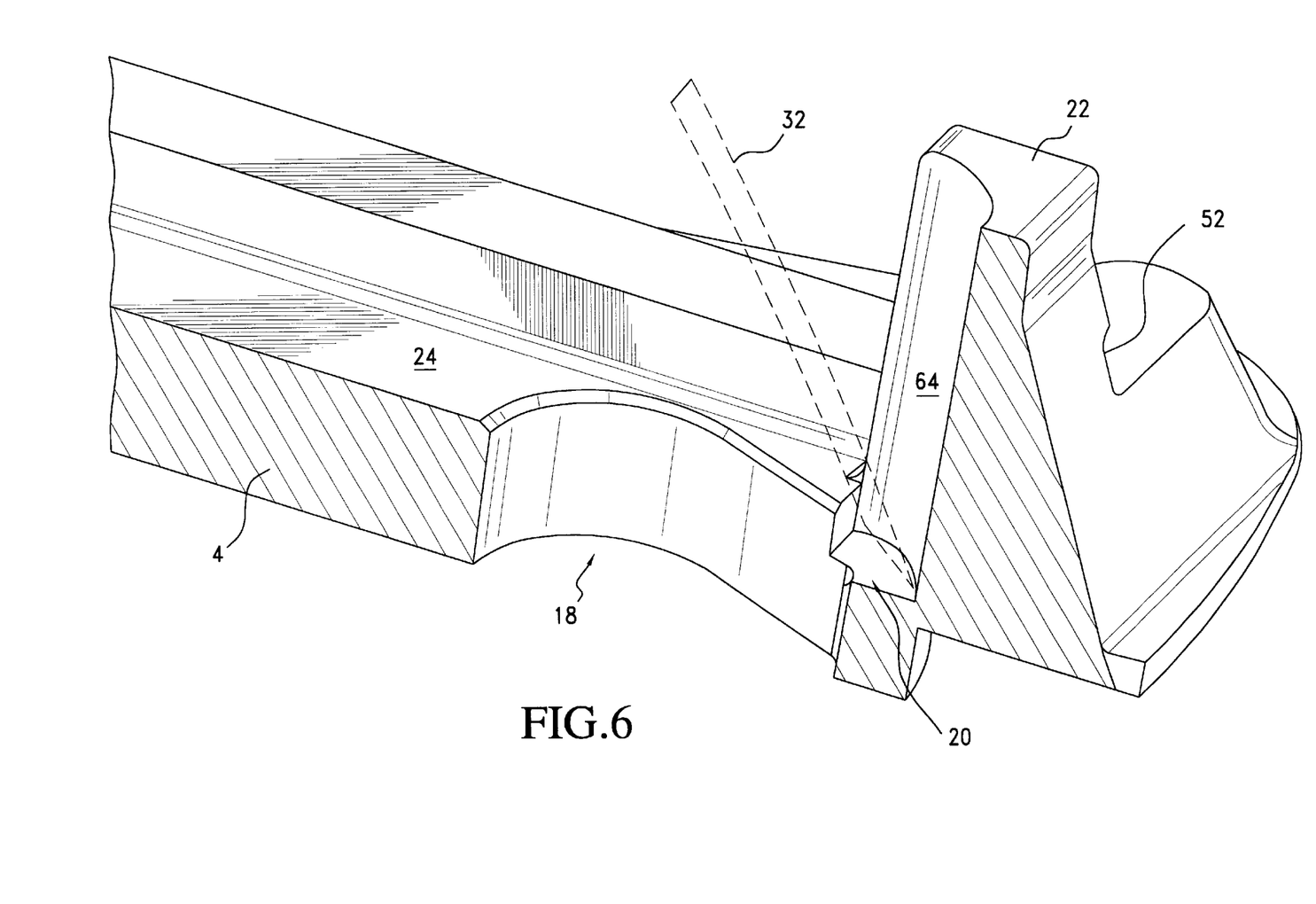
FIG. 6 is a partial exposed and enlarged view of the distal end of the base of the FIG. 1 device.
Figure 7:
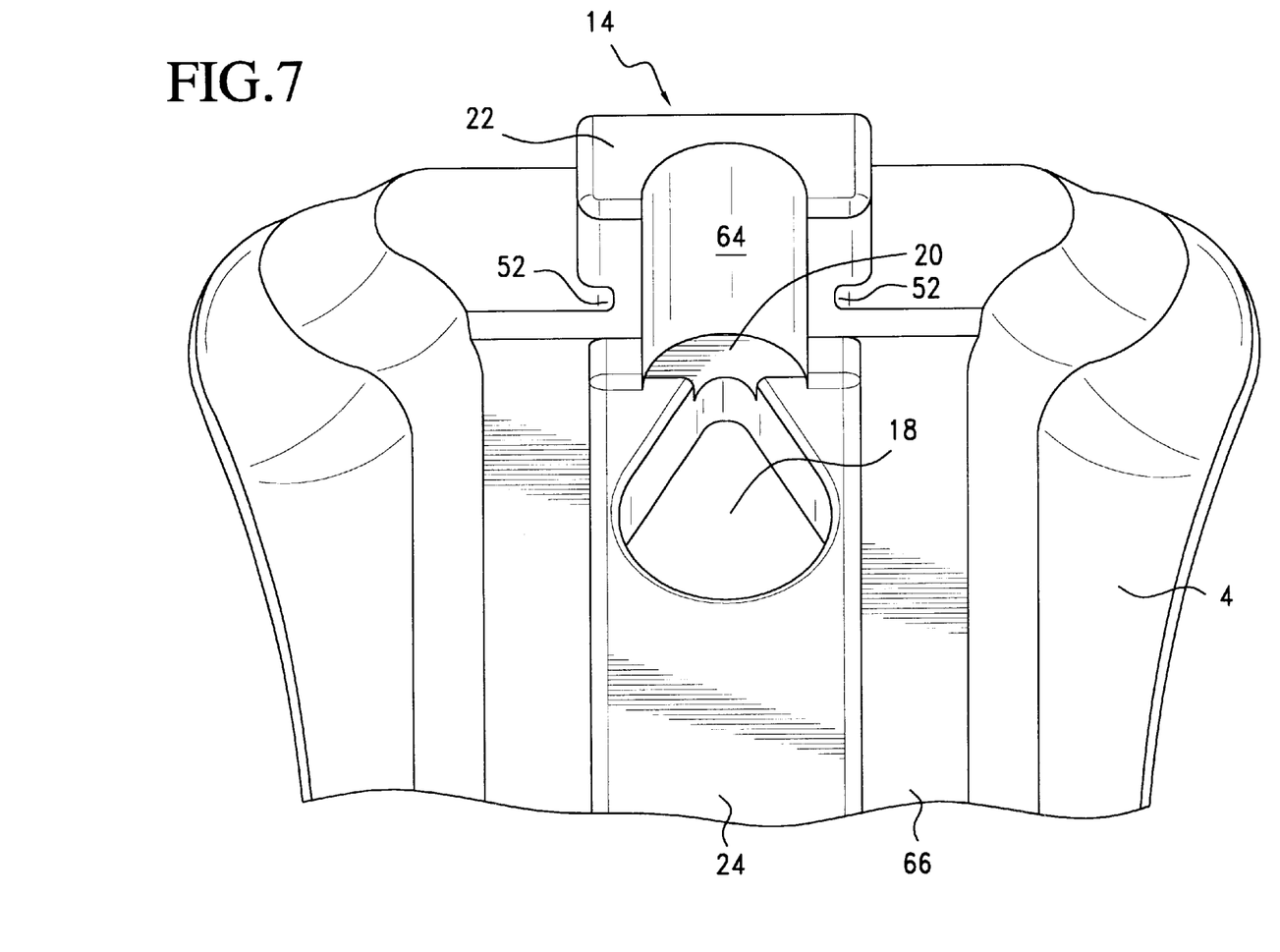
FIG. 7 is a semi-perspective top view of the distal end of the base of the device of FIG. 1.

Base 4 has a distal end 14 and a proximal end 16. As best shown in FIGS. 2 and 5, an opening or aperature 18 is provided at the distal end of base 4. As best shown in the partial cut away enlarged view of the distal end 14 of base 4 in FIGS. 6 and 7, opening 18 has formed adjacent thereto an indentation in the form of a well or catch basin 20. Well 20 is in turn surrounded or circumvented on the side away from opening 18 by a dam 22 that provides a backstop for well 20. As best shown in FIG. 6, well 20 provides a space that is below the top surface 24 of base 4 for trapping and fixedly retaining the tip of a needle. More on that later.

Figure 3:
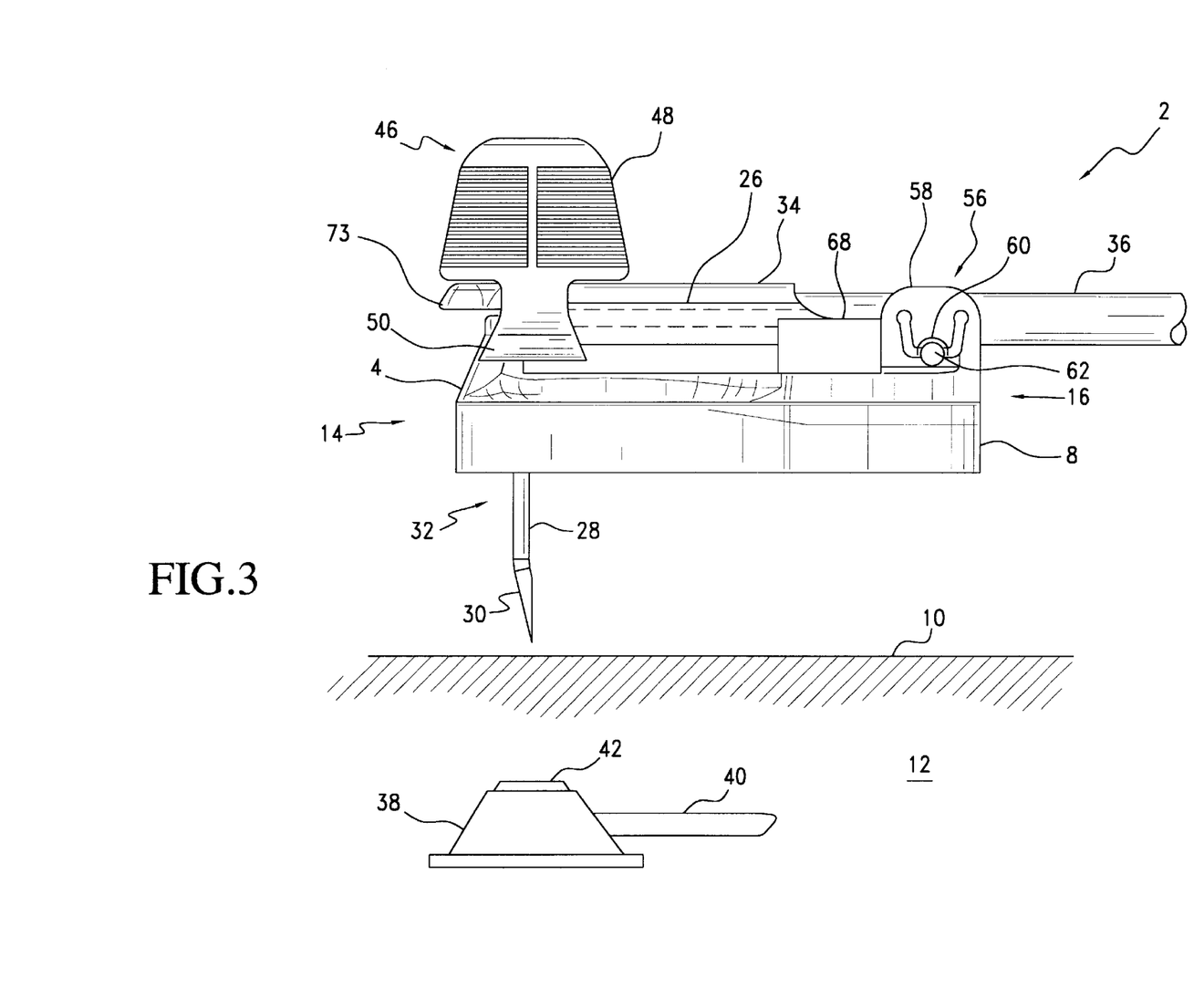
FIG. 3 is a side view of the device of FIG. 1, with reference to a patient and an intravenous infusion device implanted in the patient.

As shown in FIG. 3, the needle of the instant invention is an L-shaped right angle needle that has a first or horizontal portion 26 and a second or vertical portion 28 that is substantially orthogonal to portion 26. Needle portion 28 has a sharp tip 30 that is offset from the longitudinal axis of portion 28. For ease of discussion, since needle portions 26 and 28 are in fact joined to each other in a continuous fashion, the right angle needle as shown in FIG. 3 may simply be referred to as needle 32.

As further shown in FIG. 3, portion 26 of needle 32 is encased in the same material that makes up the base, most likely a conventional medical non-allergic synthetic plastic material so that an arm 34 is formed thereover. Connected to the arm is a fluid conduit 36, which is mated to needle portion 26, so as to effect a fluid passage through needle 32. As is well known, a medicament fluid may be diffused through conduit 36 to needle 32, and from there to an infusion port 38 implanted to patient 12. A fluid conduit 40 of port 38 in turn routes the medicament fluid to a remote site in the patient. As is further well known, port 38 has a septum 42 through which tip 30 of needle 32 may be inserted for providing fluid to port 38. As should readily be recognized, given that tip 30 of needle 32 has to pierce the skin of the patient and pass through a portion of the patient before entering septum 32 of port 30, upon withdrawal of needle 32 from the patient, tip 30 of needle 32 is contaminated and therefore may pose a health hazzard to the healthcare worker handling device 2.

Figure 1:
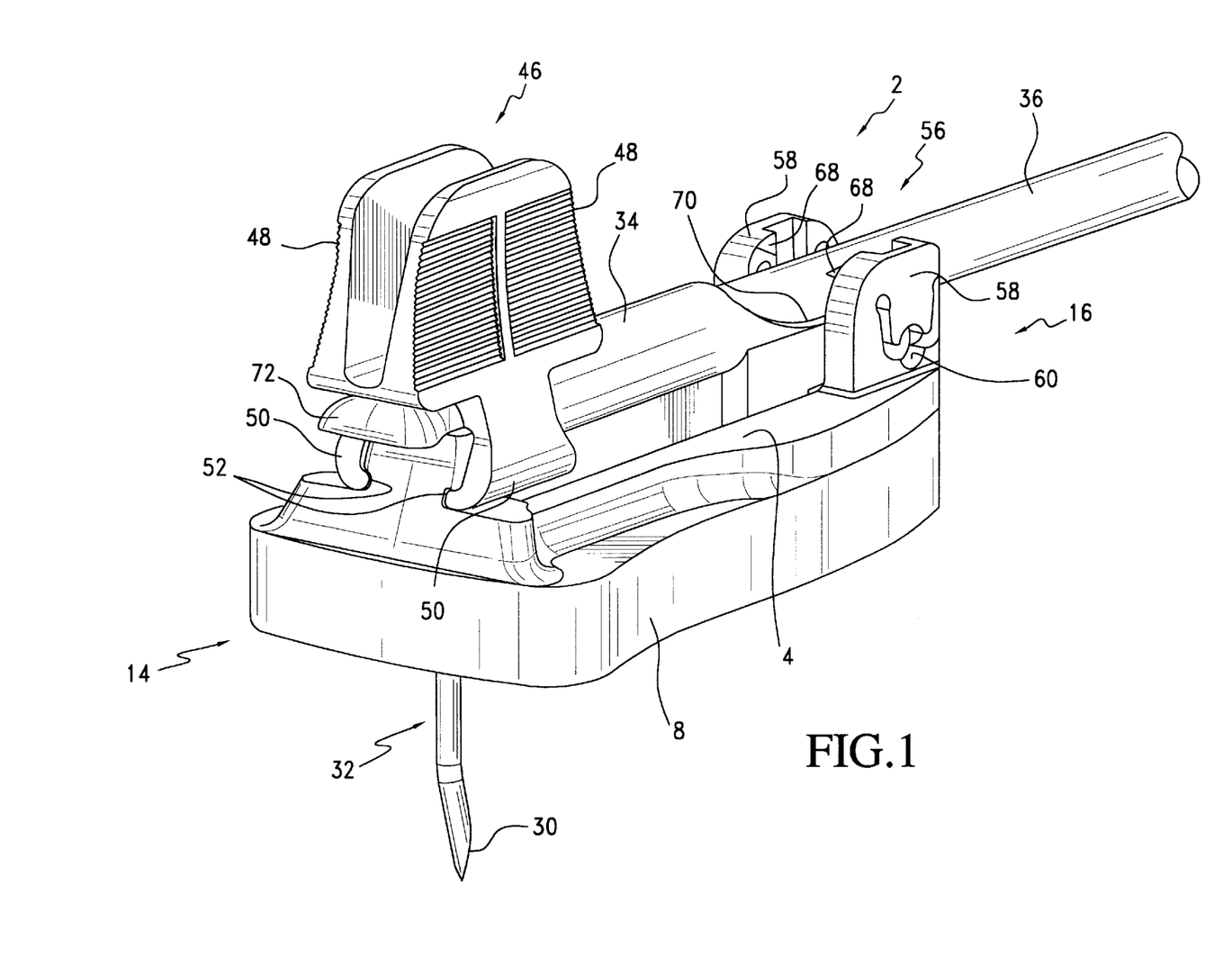
FIG. 1 is a perspective view of a first embodiment of the present invention right angle safety needle.
Figure 4:
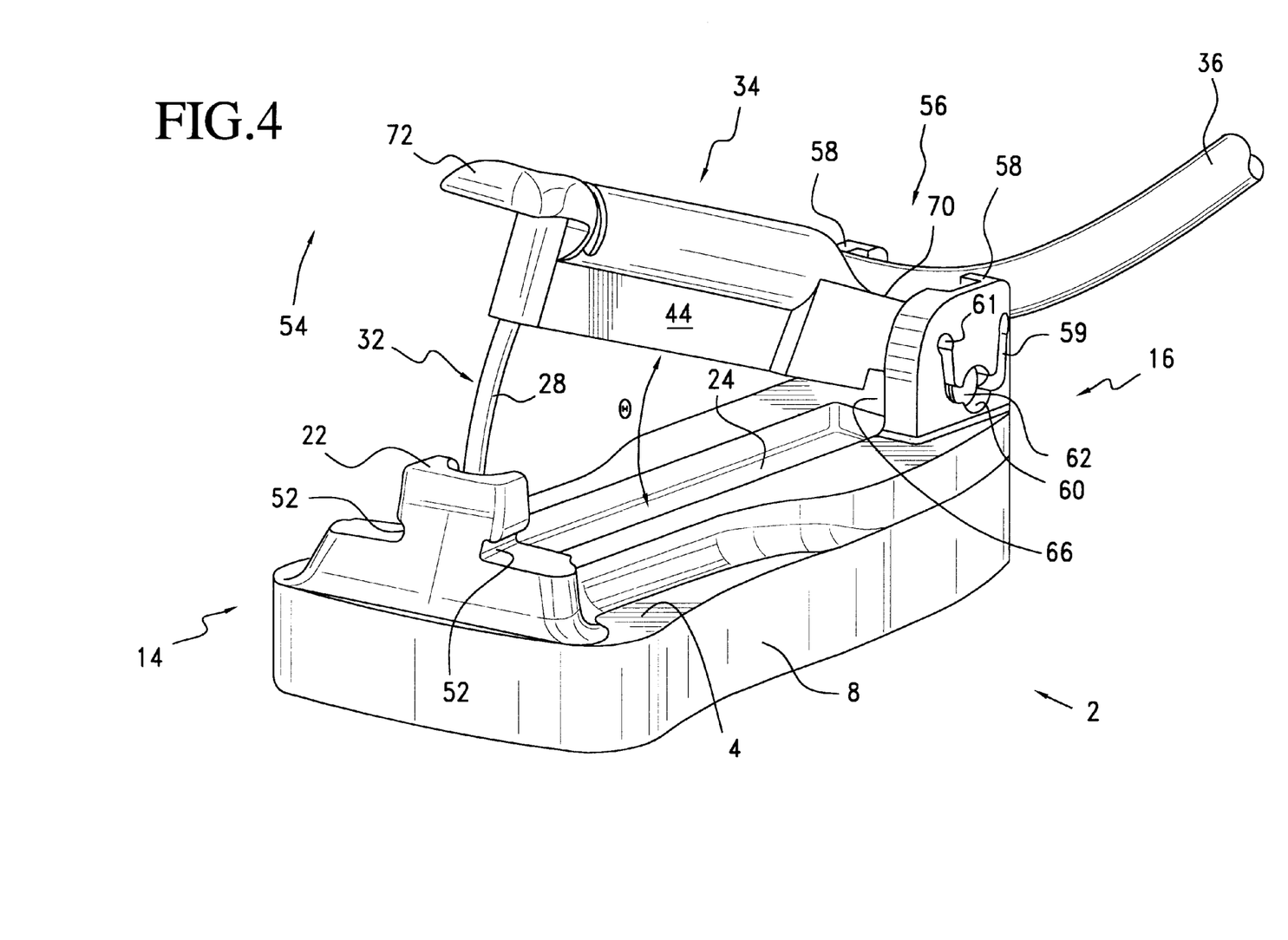
FIG. 4 is a perspective view of the device of FIG. 1 sans the positioning clip and shown in a position where the needle is trapped so as not to be reusable.

Refocusing to FIG. 4, arm 34 of device 2 is shaped such that a lower portion 44 thereof has a lower surface that comes into contact with the top surface 24 of base 4, so that when arm 34 is in the position as shown in FIGS. 1–3, the horizontal portion 26 of needle 32 is positioned in parallel along the length of base 4 while portion 28 of needle 32, which includes tip 30, extends through opening 18 in a position substantially orthogonal to base 4. It is at this first position placement of needle 32 that device 2 is used to puncture patient 12 for insertion to port 38.

Figure 8:
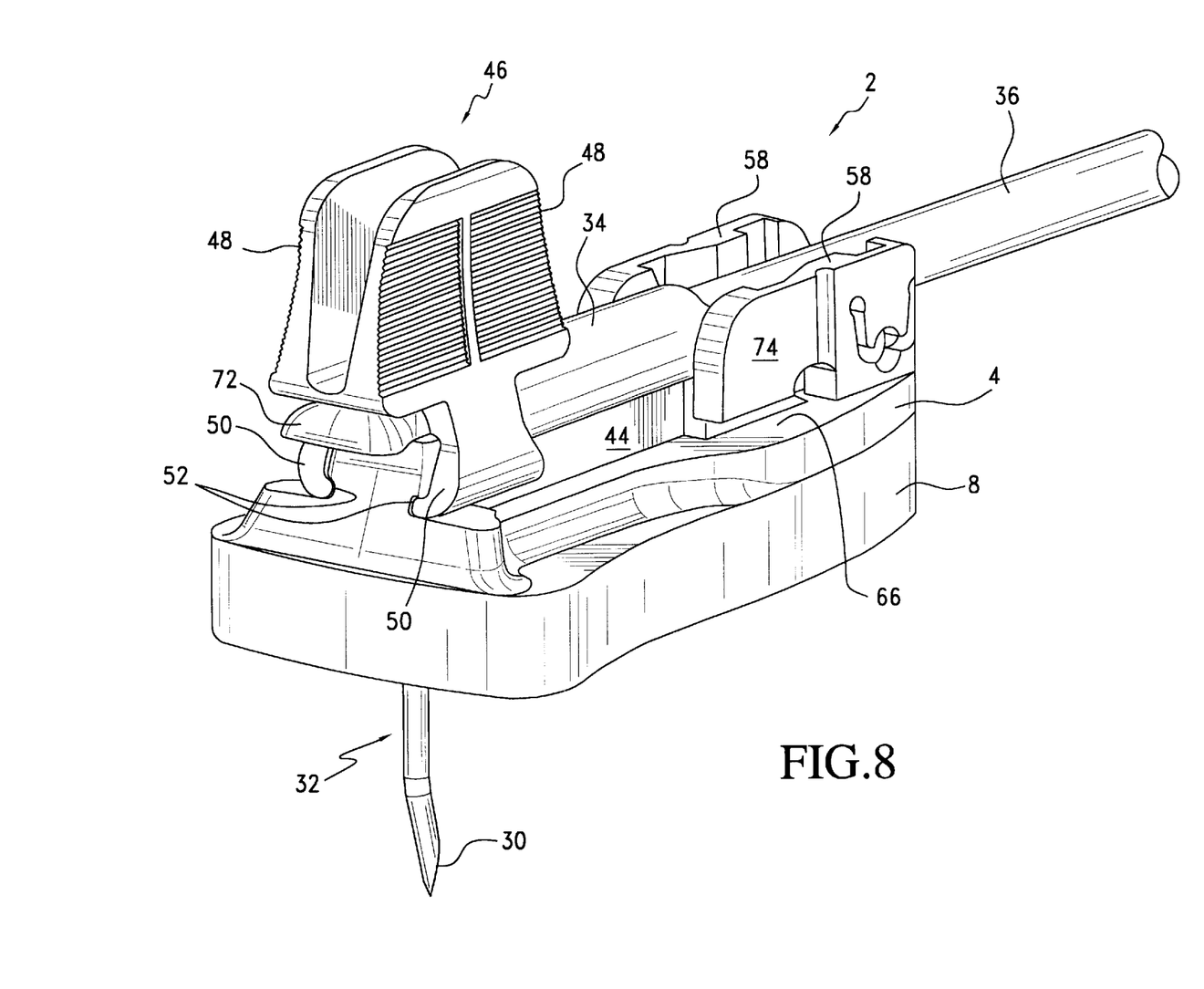
FIG. 8 is a perspective view of a second embodiment of the instant invention right angle safety needle.

To maintain needle 32 in the position as shown in FIGS. 1–3, a holding clip 46 that has two upstanding ears 48 and two gripping fingers 50 is used. As best shown in the second embodiment of the instant invention illustrated in FIG. 8, fingers 50 of holding clip 46, without any pressure applied to wings 48, would naturally be fitted to two opposing grooves 52 formed at the side of dam 22. See FIG. 4 for best illustration of grooves 52. Thus, for use in the position as shown in FIG. 3, due to holder clip 36 clampedly holding arm 34 in the horizontal position with respect to base 4 by means of fingers 50 gripping grooves 52 of dam 22, device 2 could easily be maneuvered by a healthcare worker for puncturing a patient.

Upon removal of holder clip 46 by pressure being applied against both wings 48 in an inward fashion so as to remove fingers 50 from grooves 52, arm 34 is free to be moved along the direction as indicated by directional arrow 54. This is made possible by an upright 56 that emerges from proximal end 16 of base 4. As best shown in FIGS. 1 and 4, upright 56 is U-shaped due to two upward extending sidewalls 58. Each of sidewalls 58 has a hole 60 through which two pins 62 on opposing side of arm 34 are movably inserted. Thus, opening 62 act as a pivot point about which arm 34 is rotatable. Putting it differently, horizontal portion 26 of needle 32 is rotatable about upright 56 relative to base 4. Opening 60, for ease of manufacturing and insertion of pins 62 of arm 34 thereinto, has extended at both ends thereof grooves 58 and 61.

Given that vertical portion 28 continues orthogonally from horizontal portion 26 of needle 32, when arm 34 is rotated in the direction as indicated by directional arrow 54, portion 28 of needle 32 is withdrawn from aperature 18 of base 4 until, per shown by the predetermined or preset angle θ in FIG. 4, tip 30 of needle 32 is cleared from aperture 18. At that point, due to the offset relationship of tip 30 with respect to portion 28 and the tendency of portion 28 of needle 32 to return to its natural shape relative to horizontal portion 26, tip 30 of needle 32 would tend to flex forward so that it gets entrapped within well 20, per shown by the dotted needle 32 illustrated in FIG. 6. See also the plan view of FIG. 12. The inside wall 64 of dam 22 provides a semi-circumferential backstop for tip 30 of needle 32 to thereby prevent it from any further forward movement.

To ensure that arm 34 could not be rotated beyond angle θ, the proximal end of arm 34 is so configured that an edge of its end surface 64 comes into contact with surface 66 of base 4. See FIGS. 4 and 5. Alternatively, shoulder stops 68 may be provided at the inside surfaces of the respective sidewalls 58 so that the respective edges 70 of arm 34 would coact there against to thereby prevent arm 34 from rotating beyond predetermined angle θ. See FIGS. 1 and 4. As a consequence, once needle 32 is trapped in well 20, it remains trapped in well 20 by the action of tip 30 against well 20 and backstop wall 64 on the one hand, and the coaction of the edge of back surface 64 of arm 34 against surface 66 of base 4 or the coaction of edges 70 of arm 34 against shoulder stop members 68 at sidewalls 58 of upright 56. Accordingly, once arm 34 is pivoted to the position relative to base 4 as shown in FIG. 4, needle 32, more particularly tip 30 thereof, is fixedly retained in well 20. To facilitate the rotational movement of arm 34 relative to base 4, arm 34 is provided with a front extending finger grip portion 72.

Figure 9:
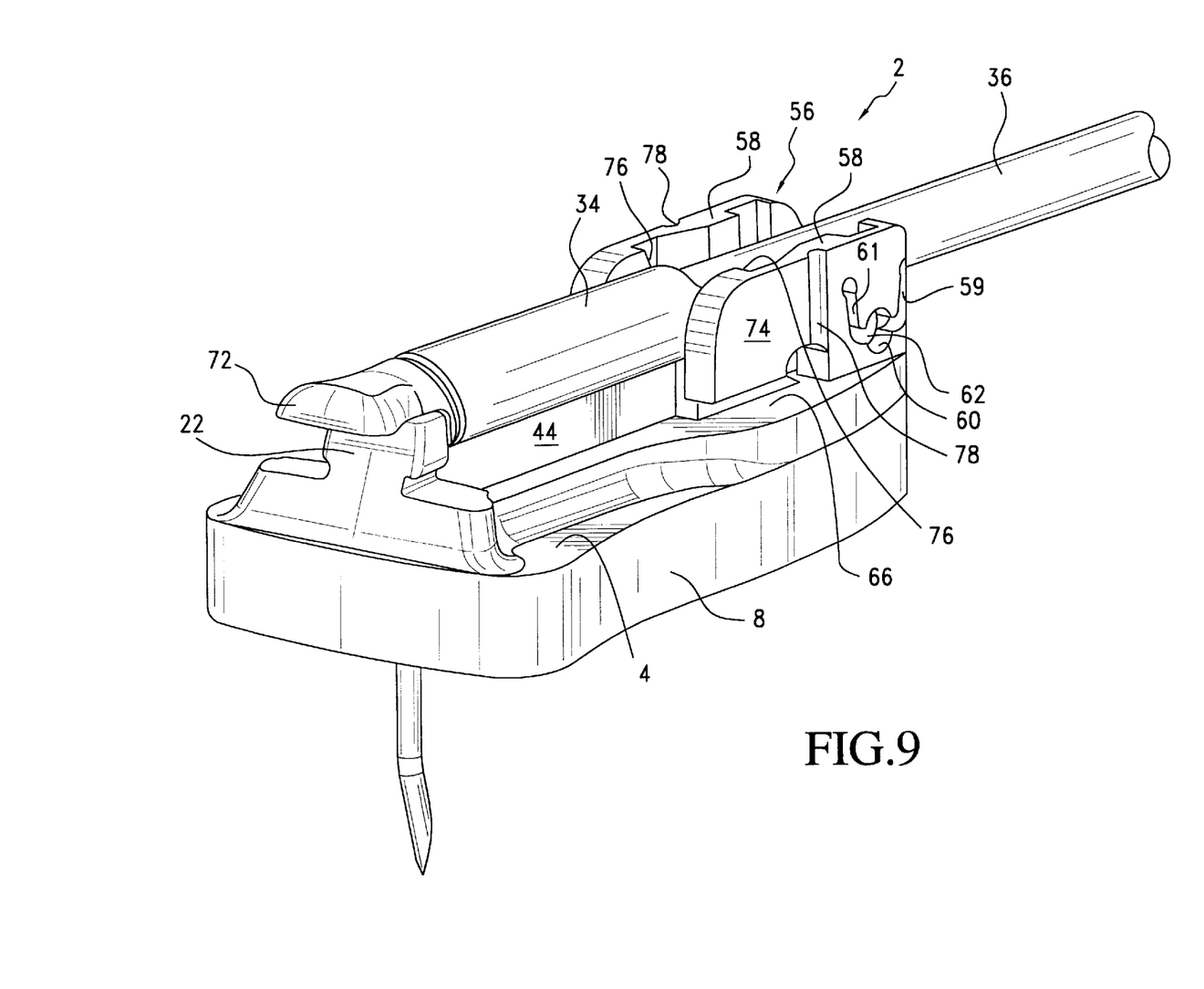
FIG. 9 is a perspective view of the device as shown in the embodiment of FIG. 8 sans the holder clip.

A second embodiment of the instant invention is shown in FIGS. 8–12. All elements that are identical or similar, or function the same, as the elements disclosed in the embodiment disclosed in FIGS. 1–7 are numbered the same. As was mentioned previously, a holder clip 46 is shown in FIG. 8 for holding in place arm 34 during the shipment of device 2 and also possibly when device 2 is first used on the patient. With holder clip 46 removed, device 2, as shown in FIG. 9, is the same as the device shown in FIGS. 1–7 but for the configuration of upright 56, more particularly its sidewalls 58, and arm 34.

As shown, each of the sidewalls 58 of the second embodiment has an extension 74 that freely extends from the main portion of sidewall 58. By making extended portion 74 free standing, a given flexibility is provided to those portions. At the inner surface of each of the extended portions 74 there is a latch or stop means 76. To enhance the flexibility of extended portion 74, each of sidewalls 58 is configured to have a groove 78 at the junction where portion 74 extends from sidewall 58, so as to provide flexible movement for extended portion 74.

Figure 10:
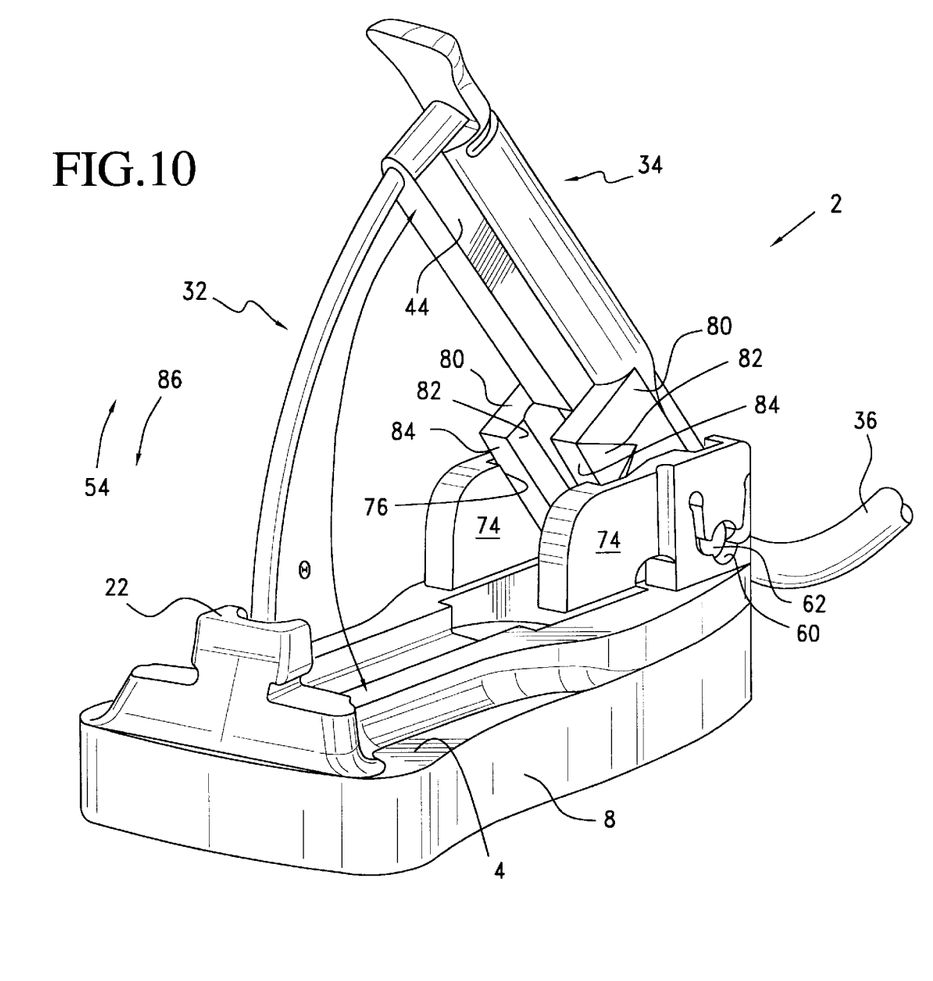
FIG. 10 is a perspective view of the device of FIG. 9 shown in a second position in which the needle is fixedly retained.
Figure 11:
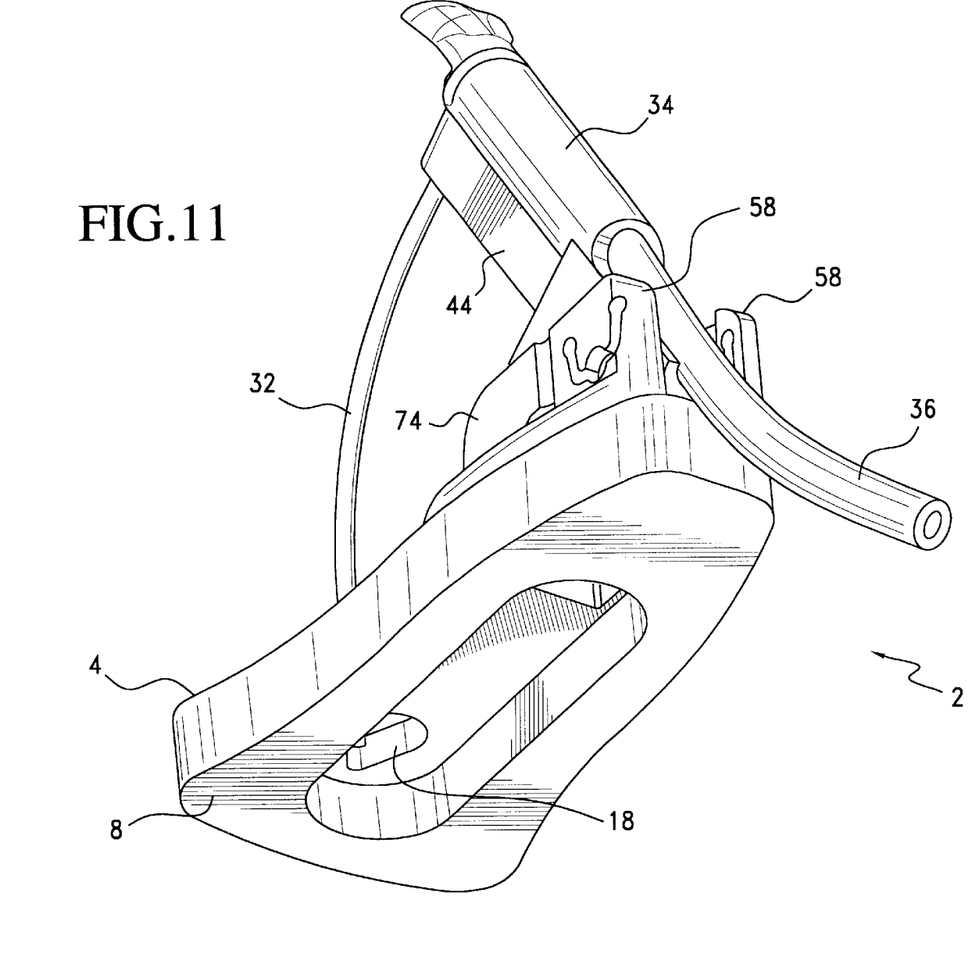
FIG. 11 is a perspective view of the device of FIG. 10 as shown from below.
Figure 12:
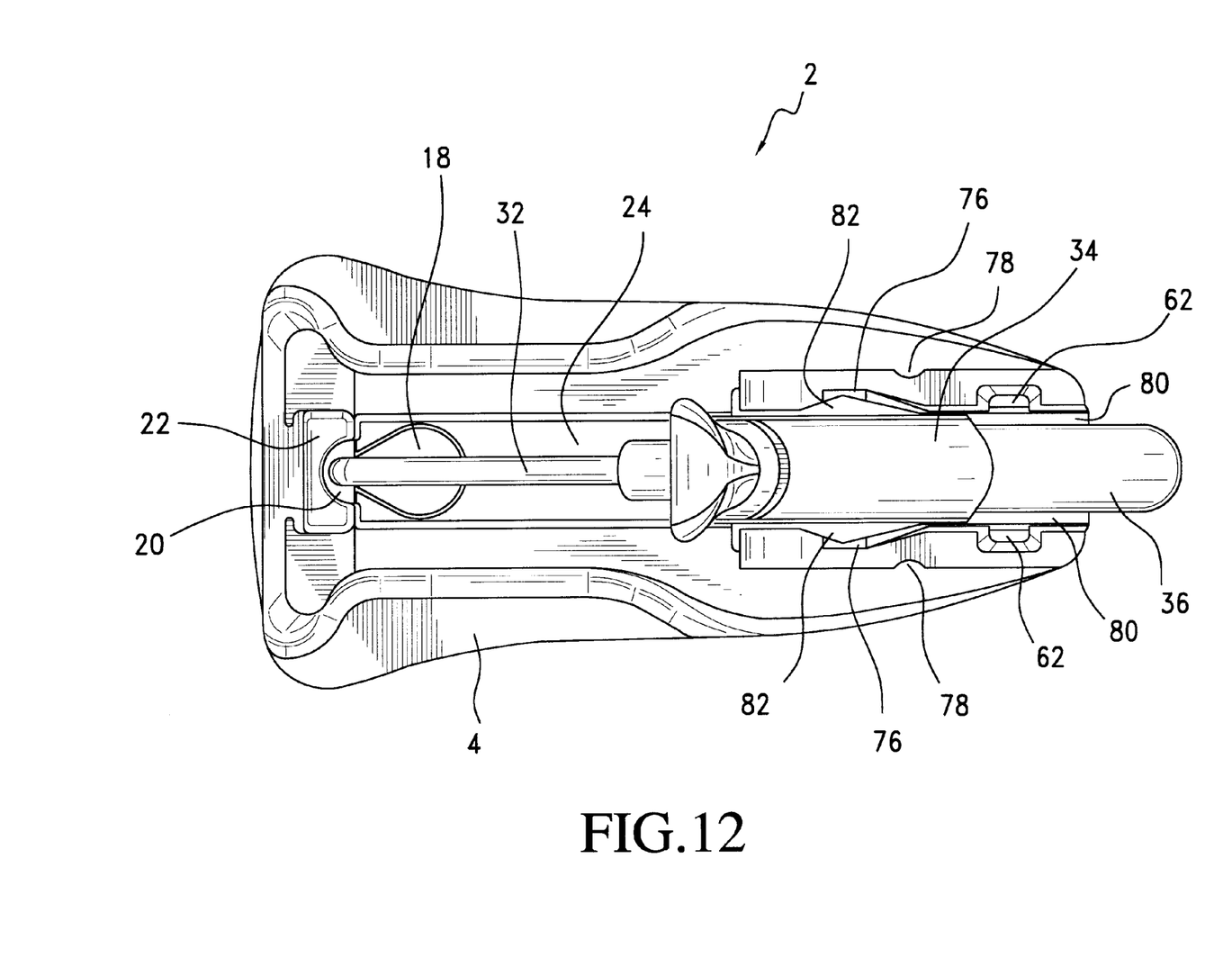
FIG. 12 is a plan view of the device of FIG. 12 particularly illustrating the retention of the tip of the needle in the well of the base.

Another difference between the embodiment of FIGS. 8–12 and the earlier embodiment is the different construction of arm 34. In particular, as best shown in FIGS. 10 and 12, arm 34 has at its aft portion two support members 80 each having a stop means in the form of a shoulder 82 that has a slanting surface that allows arm 34 to be pivoted upward along the direction as indicated by directional arrow 54. Shoulders 82 each further have a bottom surface 84 that, when arm 34 is pivoted to the predetermined angle θ relative to base 4, will coact against ledges 76 of sidewall 74 to thereby prevent any downward movement as indicated by directional arrow 86.

Thus, when coupled with the previously discussed stop mechanisms or portions at arm 34 and base 4 that prevent arm 34 from being pivoted in the upward direction, once needle 32 has been withdrawn from aperture 18 and the tip 30 thereof is entrapped within well 20, needle 32 is further prevented from moving downwards in the position as shown in FIGS. 10–12, thereby substantially eliminating any potential risk that the contaminated tip of the needle may pose to a healthcare worker. Of course, it should be appreciated that without the coacting stop portions at arm 34 and sidewall portions 74, needle 32 could nonetheless be retained in the position as shown in FIG. 10, insofar as tip 30 of needle 32 acts against the bottom of well 20 so as to prevent downward movement of arm 34. However, by providing the additional coacting stop portions at upright 56 and arm 34, an additional measure of security is provided which does not require the sole reliance of tip 30 of needle 32 to act as a stop for the downward movement of arm 34 in the direction as indicated by directional arrow 86. As can readily be seen in FIGS. 11 and 12, once needle 32 is withdrawn from opening 18 and tip 30 of needle 32 is fixedly retained in well 20, device 2 can be readily removed from the patient and discarded.

It should be appreciated that the present invention is subject to many variations, modifications and changes in detail. For example, the stop mechanisms for preventing needle 32 from further movement after it has been pivoted to a predetermined angle so that its tip is fixedly retained in the well of the device could be integrated to base 4 at different locations than those shown in the figures and discussed above. To wit, instead of acting against latches 76 at portions 74 of sidewalls 58, the extending shoulders 82 of arm 34 may be configured such that those shoulders would act against the respective top surfaces of sidewalls 58. This is possible insofar as portions 74 tends to flex back to their original positions as arm 34 is rotated in the direction indicated by directional arrow 54. Thus, portions 74 would flex back once shoulders 82 of arm 34 move beyond them. As a consequence, once returned to their natural positions, the top surfaces of portions 74 act as stops for shoulders 82 of arm 34, thereby eliminating any need for integrating latches 76 to the inside surfaces of portions 74. Similarly, instead of relying on the lower surface of back end 64 (FIG. 5) at the aft portion of arm 34 to coact against surface 66 of base 4 for stopping further upward movement of arm 34, or the stops 68 provided at sidewalls 58, other stop mechanisms at arm 32 and base 4 could also be used. For example, one way coacting mesh teeth may be provided at the inside surfaces of sidewalls 58 and the corresponding side surfaces of arm 34 so that arm 34 could only be rotated in an upward direction, at increments depending on the size of the meshing teeth.

Thus, it is the intention of the inventors that all matters described throughout this specification and shown in the accompanying drawings be interpreted as illustrative only and not in a limiting sense. Accordingly, it is intended that this invention be limited only by the spirit and scope of the hereto appended claims.

What is claimed is:

1. Apparatus, comprising:
   a base planarly contacting the skin of a patient, said base having a distal end and a proximal end;
   an opening provided at said distal end of said base;
   a catch provided adjacent said opening on said base;
   a needle pivotable relative to said proximal end of said base having a first portion positioned axially along the length of said base in a first position, and a second portion continuing from and substantially orthogonal to said first portion having a tip extending through said opening of said base in said first position;
   wherein when said needle is pivotably moved relative to said proximal end of said base to a second position, said first portion of said needle is moved to a predetermined position at an angle relative to said base and said second portion of said needle is withdrawn through said opening of said base with said tip being retained in said catch.

2. Apparatus of claim 1, further comprising:
   an upright at said proximal end of said base;
   wherein said first portion of said needle is encased in an arm having an aft portion hingedly attached to said upright, said arm being rotatable about said upright relative to said base.

3. Apparatus of claim 2, further comprising:
   stop means coacting at said arm and said upright or said base for preventing said arm from rotating past a given angle relative to said base when said tip of said needle is retained in said catch so that once said tip is retained in said catch said needle is substantially fixedly retained relative to said base and said tip could no longer be re-extended through said opening.

4. Apparatus of claim 1, further comprising:
a dam at said distal end of said base for preventing any forward movement of said tip of said needle as said tip is withdrawn from said opening and retained in said catch.

5. Apparatus of claim 2, further comprising:
stop means provided at at least said upright for preventing said arm from rotating toward said base once said tip of said needle is retained in said catch to thereby prevent said tip from being re-extended through said opening.

6. Apparatus of claim 1, wherein said catch comprises a well for receiving and retaining said tip of said needle.

7. Apparatus of claim 2, wherein said upright comprises two side walls each having a hole extending from said base, and wherein said arm includes at said aft portion two opposing pins each mated to a corresponding one of said holes for hingedly connecting said arm to said upright.

8. A safety needle device, comprising a base having an aperture through which one portion of a L-shaped needle having a sharp tip extends, said base having at least one upright to which an other portion of said L-shaped needle is hingedly connected so that said needle is rotatable about said upright relative to said base, said one portion of said needle being positioned in parallel along the length of said base and said other portion of said needle being positioned orthogonal to said base with said sharp tip extending below said base in a first position, said one portion of said needle being positioned at an angle to said base and said other portion of said needle being withdrawn from said aperture of said base when said needle is rotated about said upright to a second position.

9. The device of claim 8, further comprising a well provided at said base adjacent said aperture for receiving and retaining said tip of said needle when said other portion of said needle is withdrawn from said aperture as said needle is moved to said second position.

10. The device of claim 9, further comprising a dam to the side of said well away from said aperture for preventing said tip of said needle from moving beyond said well when said needle is being moved to said second position.

11. The device of claim 8, wherein said tip is offset from said other portion of said needle so that once said other portion of said needle is withdrawn and said tip clears said aperture, said tip is automatically biased away from said aperture into said well.

12. The device of claim 8, wherein said upright comprises a U-shaped member having two side walls and wherein said one portion of said needle is encased in an arm pivotably mounted to said U-shaped member so as to be rotatable thereabout relative to said base.

13. The device of claim 9, wherein said one portion of said needle is encased in an arm pivotably mounted to said upright so as to be rotatable thereabout relative to said base, said device further comprising stop means coacting at said arm and said upright or said base for preventing said arm from rotating past said angle relative to said base when said tip of said needle clears said aperture and is retained in said well.

14. The device of claim 9, wherein said one portion of said needle is encased in an arm pivotably mounted to said upright so as to be rotatable thereabout relative to said base, said device further comprising stop means provided at at least said upright for preventing said arm from rotating toward said base once said tip of said needle is retained in said well so that said tip is prevented from being re-extended through said aperture.

15. In combination, a base for contacting the skin of a patient having an upright at a proximal end and an aperture at a distal end, a L-shaped needle having one portion encased in an arm pivotably connected to said upright and an other portion having a tip for piercing the skin of the patient extending through said aperture in a first position, a well provided at said base adjacent said aperture at said distal end of said base for receiving and retaining said tip when said needle is pivoted to a second position whereby said one portion of said needle is positioned at a predetermined angle relative to said base and said other portion of said needle is withdrawn from said aperture, a dam at said base proximate to said well for preventing said tip of said needle from moving beyond said well when said needle is moved to said second position, and stop means at said arm and said base for preventing further movement of said needle relative to said base once said other portion of said needle is withdrawn from said aperture and said tip is retained in said well.

16. The combination of claim 15, wherein said stop means comprises coacting portions at said arm and said upright or said base for preventing said arm from rotating past said predetermined angle relative to said base when said tip of said needle is retained in said well to thereby prevent said tip from being re-extended through said aperture.

17. The combination of claim 15, wherein said stop means comprises a stop portion at at least said upright for preventing said arm from rotating toward said base once said tip of said needle is retained in said well so that said tip is prevented from being re-extended through said aperture.

18. The combination of claim 15, wherein said stop means comprises first stop portions coacting at said arm and said upright or said base for preventing said arm from rotating past said predetermined angle relative to said base and a second stop portion at at least said upright for preventing said arm from rotating toward said base once said tip of said needle is retained in said well.

* * * * *